United States Patent [19]
Bax et al.

[11] Patent Number: 5,313,666
[45] Date of Patent: May 24, 1994

[54] FACIAL SUN SHIELD APPARATUS

[76] Inventors: Vickie R. Bax; Dale F. Bax, both of 403 Southeast Ter., California, Mo. 65018

[21] Appl. No.: 877,793

[22] Filed: May 4, 1992

[51] Int. Cl.$^5$ .............................................. A42B 1/18
[52] U.S. Cl. .............................................. 2/9; 52/87; 135/86
[58] Field of Search ............. 2/9, 10, 11, 12, 15, 2/177, 185 R, 199, 425, 426, 430, 432, 439, 447, 451, 452, 453, 454; 47/28.1 C, 19 R; 52/86; 135/87, 16, 96, 104

[56] References Cited

U.S. PATENT DOCUMENTS

| | | | |
|---|---|---|---|
| 3,042,053 | 7/1962 | Gabriel | 135/87 |
| 3,075,536 | 1/1963 | Parker | 135/87 |
| 4,002,333 | 1/1977 | Gotoh | 52/86 |
| 4,379,349 | 4/1983 | Larson | 2/9 |
| 4,558,969 | 12/1985 | FitzSimons | 52/86 |
| 4,644,706 | 2/1987 | Stafford et al. | 52/86 |
| 4,821,353 | 4/1989 | Neri | 135/87 X |
| 4,867,187 | 9/1989 | Divine | 135/16 |
| 4,987,707 | 1/1991 | Kiselev et al. | 52/86 X |
| 5,116,288 | 5/1992 | Kondo et al. | 2/177 |
| 5,143,107 | 9/1992 | Kelley | 135/16 |

Primary Examiner—Clifford D. Crowder
Assistant Examiner—Jeanette E. Chapman
Attorney, Agent, or Firm—Leon Gilden

[57] ABSTRACT

A plurality of spaced mounting blocks pivotally support an arcuate shield therebetween projecting above the mounting blocks defining a concave surface in confronting relationship relative to a support web directed between the boxes. A first of said mounting box is arranged to include a radio, with a second arranged to provide for a timer mechanism to permit timing of a sun bathing event, with the shield affording protection of a facial surface of an individual relative to sun rays. A modification of the invention includes a spray medium directed onto an individual's face to enhance cooling during a sun bathing event.

6 Claims, 4 Drawing Sheets

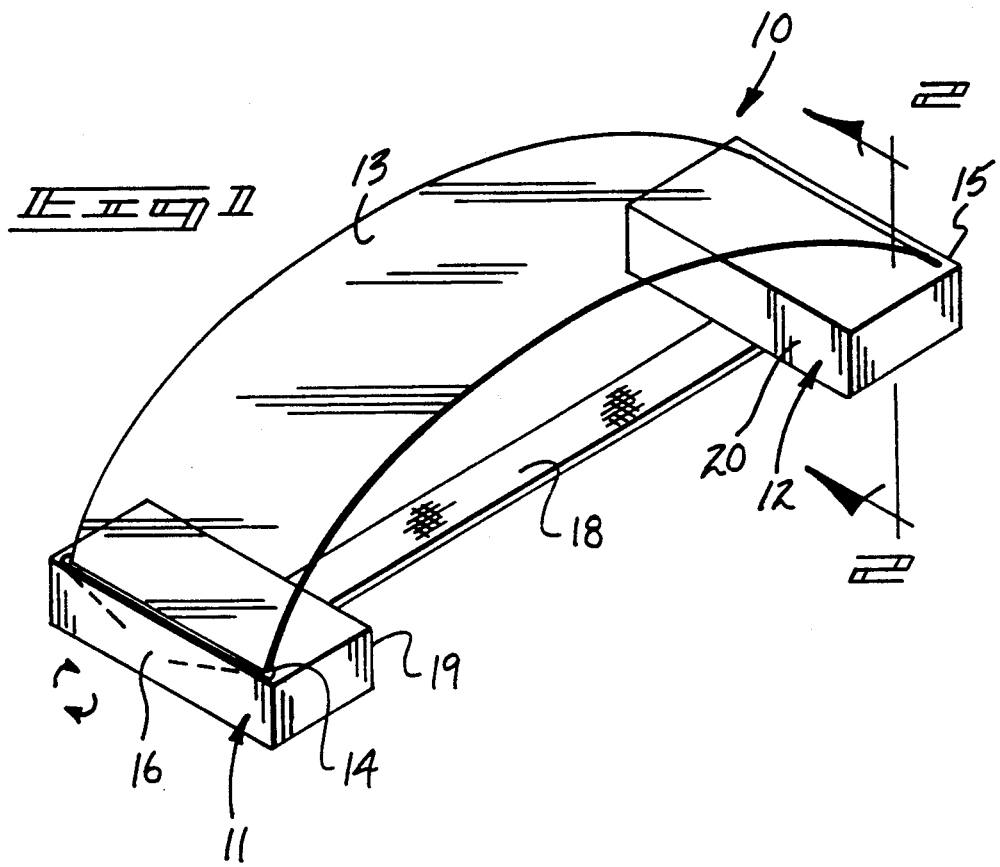
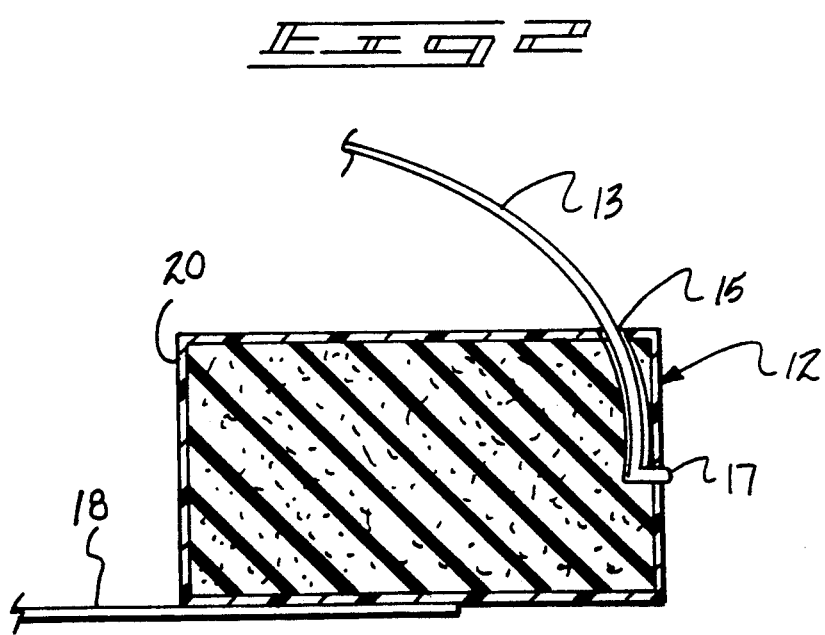

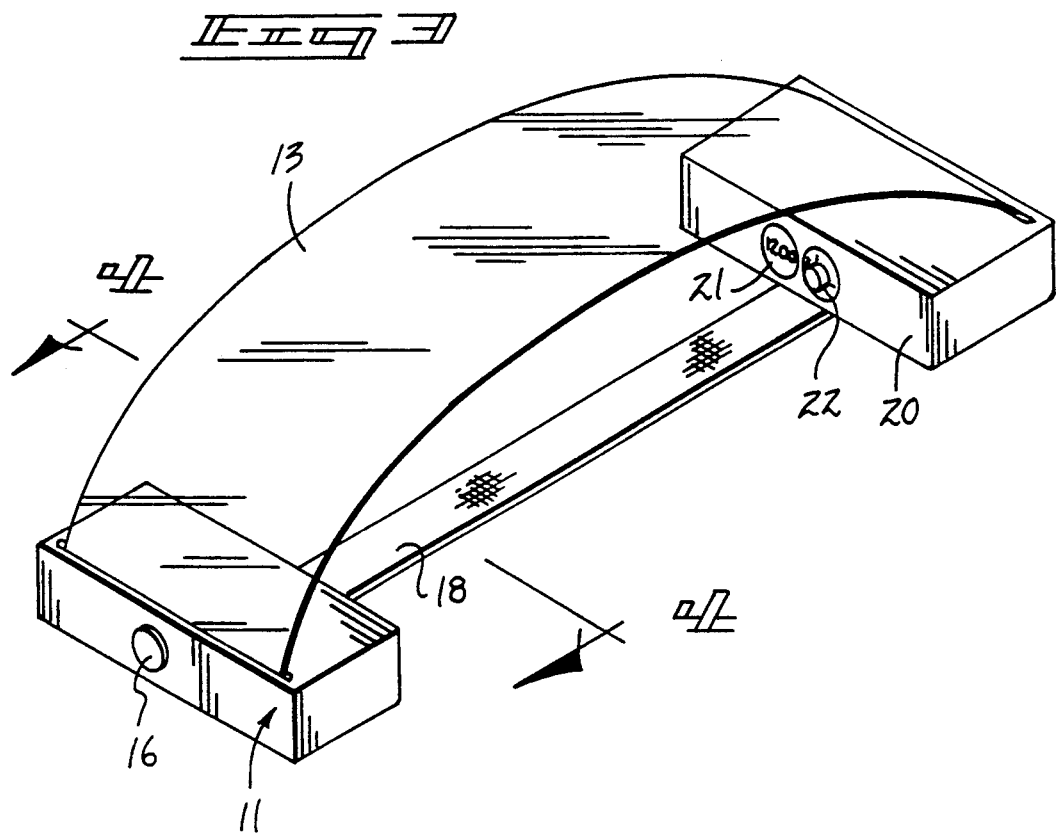
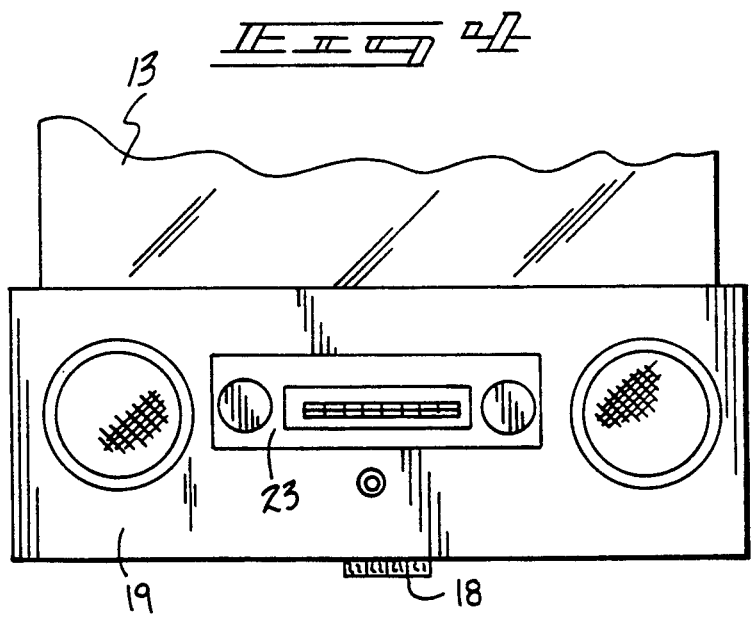

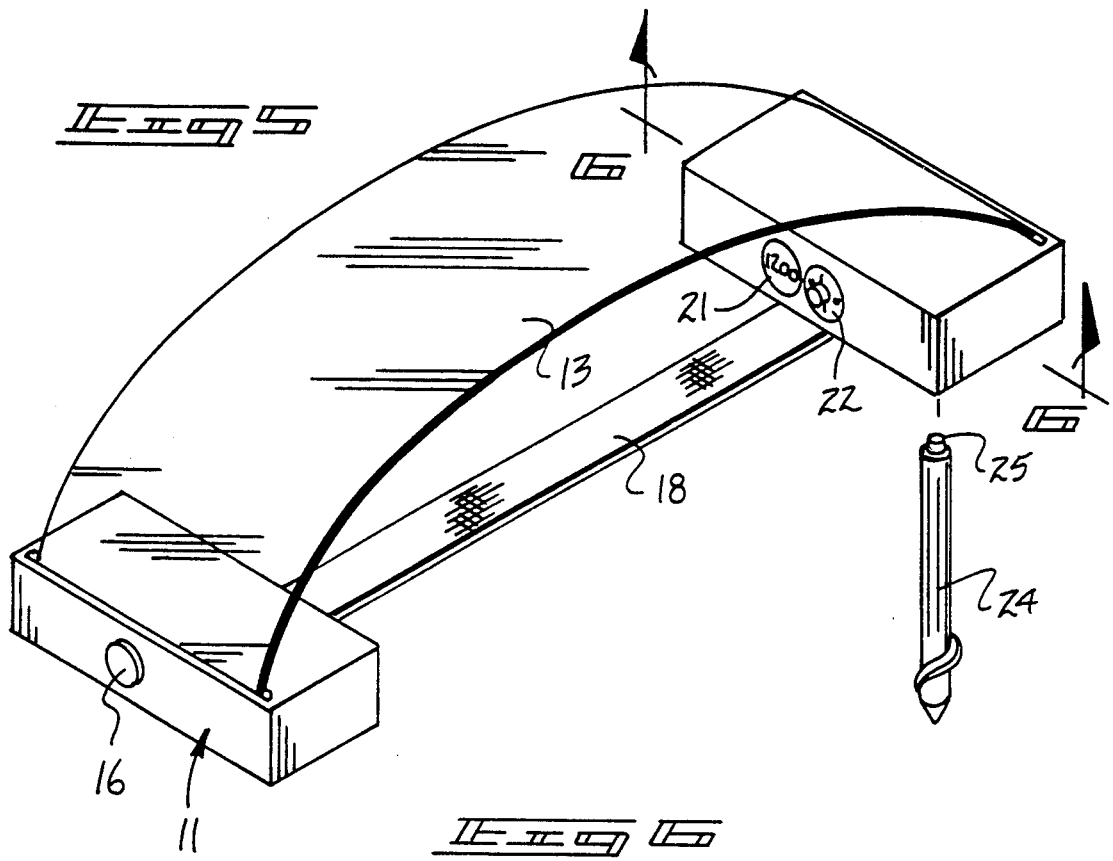
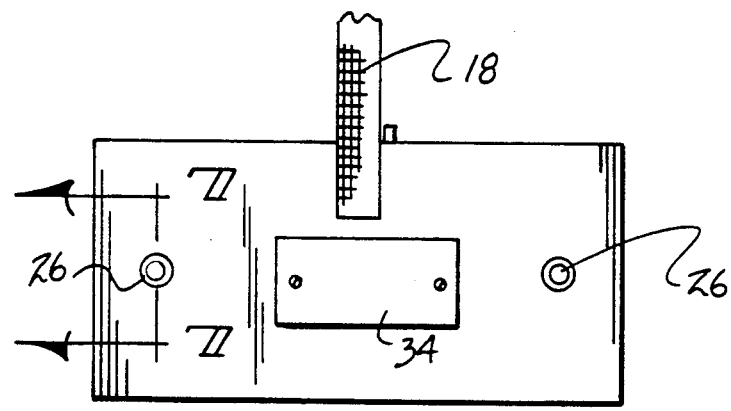
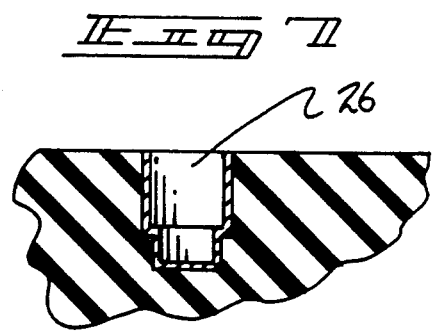

FACIAL SUN SHIELD APPARATUS

BACKGROUND OF THE INVENTION

1. Field of the Invention

The field of invention relates to shield apparatus, and more particularly pertains to a new and improved facial sun shield apparatus wherein the same affords protection to an individual's face.

2. Description of the Prior Art

Sun bathing of various types is known to enhance facial wrinkling, wherein the instant invention attempts to overcome deficiencies of the prior art to afford protection to an individual's face during a sun bathing event to avert the ill effects of sun bathing to an individual's facial regions. A prior art sun shield structure is addressed in the U.S. Pat. No. 4,109,322 to Ott having a sun shield formed with a flat insulating member mounted above and pivotally spaced relative to a head band worn by an individual.

U.S. Pat. No. 4,379,349 to Larson sets forth a sun shield arranged for positioning over an individual's face having an arcuate shield structure including spaced wire support loops directed from opposed end portions of the shield structure.

U.S. Pat. No. 4,958,652 to Mays sets forth a portable sun shade member of planar construction easily erected to permit rectilinear configuration to afford a sheltering member relative to an individual during a sun bathing event.

U.S. Pat. No. 4,837,862 to Heil sets forth a sun, rain, and wind deflector worn above an individual's facial regions.

U.S. Pat. No. 4,993,081 to Fulghum sets forth a flexible sun shield arranged for securement relative to a helmet structure.

As such, it may be appreciated that there continues to be a need for a new and improved facial sun shield apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of sun shield apparatus now present in the prior art, the present invention provides a facial sun shield apparatus wherein the same is arranged for mounting above an individual's face during a sun bathing event. As such, the general purpose of the present invention, which will be described subsequently in greater detail, is to provide a new and improved facial sun shield apparatus which has all the advantages of the prior art sun shield apparatus and none of the disadvantages.

To attain this, the present invention provides a plurality of spaced mounting blocks pivotally supporting an arcuate shield therebetween projecting above the mounting blocks defining a concave surface in confronting relationship relative to a support web directed between the boxes. A first of said mounting box is arranged to include a radio, with a second arranged to provide for a timer mechanism to permit timing of a sun bathing event, with the shield affording protection of a facial surface of an individual relative to sun rays. A modification of the invention includes a spray medium directed onto an individual's face to enhance cooling during a sun bathing event.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved facial sun shield apparatus which has all the advantages of the prior art sun shield apparatus and none of the disadvantages.

It is another object of the present invention to provide a new and improved facial sun shield apparatus which may be easily and efficiently manufactured and marketed.

It is a further object of the present invention to provide a new and improved facial sun shield apparatus which is of a durable and reliable construction.

An even further object of the present invention is to provide a new and improved facial sun shield apparatus which is susceptible of a low cost of manufacture with regard to both materials and labor, and which accordingly is then susceptible of low prices of sale to the consuming public, thereby making such facial sun shield apparatus economically available to the buying public.

Still yet another object of the present invention is to provide a new and improved facial sun shield apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention.

FIG. 2 is an orthographic view, taken along the lines 2—2 of FIG. 1 in the direction indicated by the arrows.

FIG. 3 is an isometric illustration of the invention illustrating positioning of a timer mechanism and radio within the organization.

FIG. 4 is an orthographic view, taken along the lines 4—4 of FIG. 3 in the direction indicated by the arrows.

FIG. 5 is an isometric illustration of the invention illustrating the use of the anchor structure in cooperation with the invention.

FIG. 6 is an orthographic view, taken along the lines 6—6 of FIG. 5 in the direction indicated by the arrows.

FIG. 7 is an orthographic view, taken along the lines 7—7 of FIG. 6 in the direction indicated by the arrows.

DESCRIPTION OF THE PREFERRED EMBODIMENT

Figure 8:
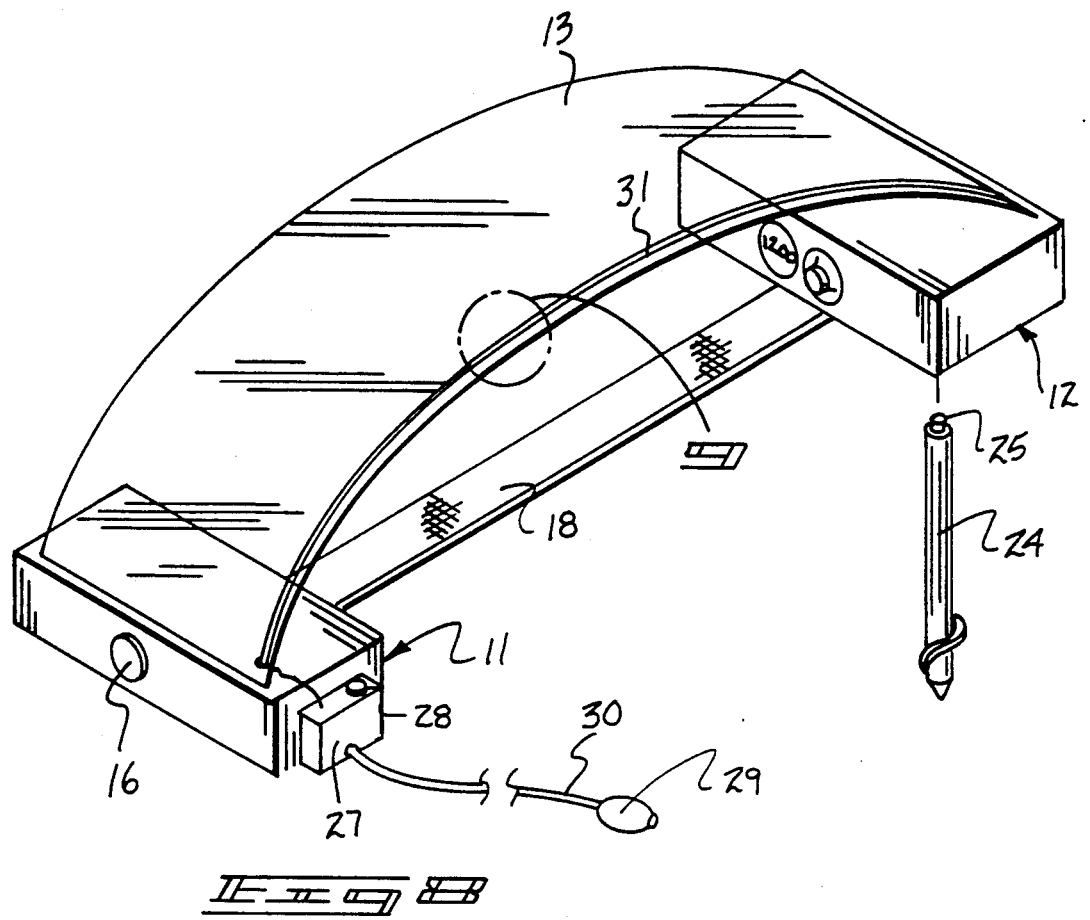
FIG. 8 is an isometric illustration of the invention illustrating the use of a spray conduit utilized by the invention.
Figure 9:
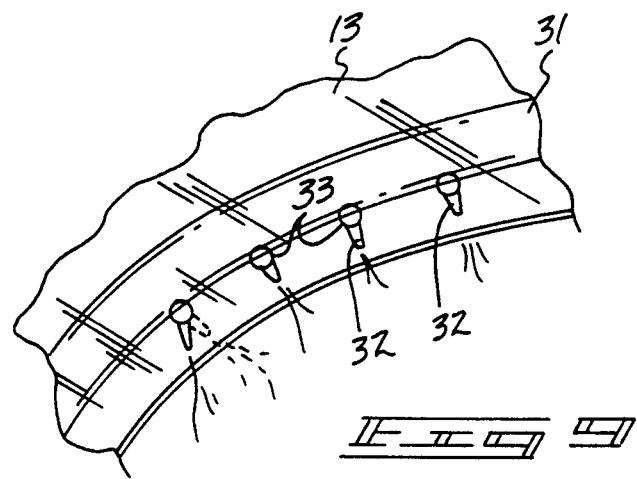
FIG. 9 is an isometric illustration, somewhat enlarged, of section 9 as set forth in FIG. 8.

With reference now to the drawings, and in particular to FIGS. 1 to 9 thereof, a new and improved facial sun shield apparatus embodying the principles and concepts of the present invention and generally designated by the reference numeral 10 will be described.

More specifically, the facial sun shield apparatus 10 of the instant invention essentially comprises a first support block 11 spaced from a second support block 12. An ultraviolet shield web 13 is arranged having a convex outer surface and a concave interior surface arranged in confronting relationship overlying the first and second support blocks 11 and 12. The web 13 is pivotally received within the first block top wall slot 14 and within a second block top wall slot 15, with the slots arranged in a parallel relationship relative to one another. A first shield pivot axle dial 16 directed through an exterior side wall of the first support block 11 is arranged for pivotally mounting the shield relative to the first and second support blocks, with the second block pivotally mounted about a second shield pivot axle 17, as illustrated in FIG. 2. A connecting strap 18 mounted to a bottom surface of the first and second support block respectively is orthogonally directed between the first and second support block, and more specifically relative to the first block interior side wall 19 and the second block interior side wall 20 that are arranged in a confronting relationship relative to one another, as illustrated in FIG. 1. A clock 21 and a timer dial 22 is mounted within the second support block 12 and in the second block interior side wall 20, in a manner as illustrated in FIG. 3, as an optional component for use of the invention to permit timing of a sun bathing event when an individual's head is positioned between the connection strap 18 below the shield web 13. It should be noted that a bottom surface of the second block 12 includes a battery cover plate 34 to permit access to batteries therebelow (not shown) of commercial availability for providing electrical energy for the clock 21 and associated timer. Similarly, such battery access is afforded relative to the radio structure 23, as illustrated in FIG. 4, mounted to the interior face 19 of the first support block 11. Further, a radio 23 is arranged for mounting within the first block's interior side wall 19, as illustrated in FIG. 4, to provide for entertainment and amusement during a sun bathing event.

The FIG. 5 illustrates the use of the anchor spikes 24 for use by the invention, wherein one is illustrated, it is understood that a plurality of such spikes can be utilized with each of the support blocks, wherein for purposes of illustration, only one such spike is indicated having an anchor spike upper shank tip 25 complementarily received within a tip receiving socket 26 through a bottom surface of an associated support block. The sockets 26 are orthogonally directed into the support block to properly position the support blocks relative to one another when positioned upon a sand surface. It should be noted that a lower portion of the spike 24 is formed with an externally positioned thread to enhance mounting within an underlying beach surface if required.

The FIG. 8 illustrates the further use of the first support block 11 having a fluid reservoir 27 mounted thereto, with the fluid reservoir including a reservoir fill cap 28 to permit selective filling of the fluid reservoir with fluid such as water. A squeeze bulb 29 is in pneumatic communication with the reservoir 27 through a squeeze bulb connecting conduit 30. From the fluid reservoir 27, a dispensing conduit 31 is directed coextensively along the interior surface of the shield web 13 overlying the connecting strap 18. The dispensing conduit 31 includes a plurality of nozzles 32 that are pivotally mounted relative to a socket base 33 to permit orientation of the nozzles relative to an individual positioned below the shield web 13 over the connecting strap 18.

Modifications of the invention for convenience and effectiveness are contemplated such as the sockets 26 being formed of a ferrous metallic liner and the shank tips 25 formed of a magnetic material to magnetically adhere the shank tips relative to the sockets.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A facial sun shield apparatus, comprising,
   a first support block spaced from a second support block, the first support block having a first block top wall, the second support block having a second block top wall, the first block top wall including a first slot, the second block top wall including a second slot, with the first slot and the second slot arranged in a parallel relationship relative to one another, and
   a shield web having a convex outer surface and a concave interior surface directed into the first support block through the first slot, and directed into the second support block through the second slot, and
   a first pivot axle dial orthogonally oriented relative to the first slot mounts the shield web within the first support block, a second shield pivot axle orthogonally directed through the second slot within the second support block pivotally mounts the shield web within the second block, and
   a flexible elongate connecting strap directed in fixed communication between the first support block and second support block.

2. An apparatus as set forth in claim 1 wherein the first support block includes a first block bottom wall, the second support block includes a second block bottom wall, wherein the connecting strap is mounted at a first end to the first support block bottom wall, and the connecting strap mounted at a strap second end to the second block bottom wall.

3. An apparatus as set forth in claim 2 wherein the first support block includes a first support block interior face, and the second support block includes a second support block interior face, with the first interior face and the second interior face arranged in confronting relationship relative to one another, the first interior face including a radio mounted therethrough, the second interior face including a clock and timer mechanism mounted therethrough.

4. An apparatus as set forth in claim 3 wherein at least said second support block bottom wall includes a plurality of sockets directed into the second support block through the second support block bottom wall, with the sockets orthogonally oriented relative to the second support block bottom wall, and at least one anchor spike having an upper shank tip complementarily received within at least one of said sockets, and said sockets are formed of a ferrous magnetic material, and the shank tip is formed of a ferromagnetic material to magnetically adhere the shank tip within the at least one of said sockets.

5. An apparatus as set forth in claim 4 wherein the first support block includes a fluid reservoir fixedly mounted thereto, the fluid reservoir including a connecting conduit directed into the fluid reservoir, with a squeeze bulb mounted to the connecting conduit spaced from the fluid reservoir to permit pressurizing of the fluid reservoir, and a dispensing conduit in fluid communication with the fluid reservoir directed from the fluid reservoir and mounted to the interior surface of the shield web in confronting relationship relative to the connecting strap, with the dispensing conduit including a plurality of spaced nozzles mounted therealong.

6. An apparatus as set forth in claim 5 wherein each nozzle includes a socket base pivotally mounting each nozzle relative to the dispensing conduit.

* * * * *